United States Patent [19]

Abts

[11] 4,365,515
[45] Dec. 28, 1982

[54] ULTRASONIC SENSING

[75] Inventor: Leigh R. Abts, Providence, R.I.

[73] Assignee: Micro Pure Systems, Inc., North Providence, R.I.

[21] Appl. No.: 187,615

[22] Filed: Sep. 15, 1980

[51] Int. Cl.³ ..................... G01N 24/00; G01N 29/00
[52] U.S. Cl. ..................................... 73/632; 310/334; 310/335
[58] Field of Search ............... 73/642, 644, 861.18, 73/597, 861.25, 632; 310/335, 334

[56] References Cited

U.S. PATENT DOCUMENTS

| | | | |
|---|---|---|---|
| 2,770,795 | 11/1956 | Peterson | 73/861.25 X |
| 2,967,957 | 1/1961 | Massa | 310/335 |
| 3,233,449 | 2/1966 | Harmon | 73/642 X |
| 3,510,698 | 5/1970 | Massa | 310/335 X |
| 3,710,151 | 1/1973 | Massa et al. | 310/341 X |
| 3,774,717 | 11/1973 | Chodorow | 73/597 X |
| 3,781,576 | 12/1973 | Runde et al. | 73/644 X |
| 3,816,773 | 6/1974 | Baldwin et al. | 310/8.1 |
| 3,821,834 | 7/1974 | McElroy | 29/25.35 |
| 3,890,423 | 6/1975 | Zacharias, Jr. | 310/335 |
| 3,898,840 | 8/1975 | McElroy | 73/644 |
| 3,935,484 | 1/1976 | Lescher et al. | 310/327 |
| 3,950,660 | 4/1976 | McElroy | 73/644 X |
| 4,068,521 | 1/1978 | Cosentino et al. | 73/19 |
| 4,080,837 | 3/1978 | Alexander et al. | 73/597 X |
| 4,112,773 | 9/1978 | Abts | 73/642 |
| 4,118,649 | 10/1978 | Shwartzman et al. | 310/337 |
| 4,190,783 | 2/1980 | Massa | 310/335 X |
| 4,214,484 | 7/1980 | Abts | 73/632 |
| 4,297,607 | 10/1981 | Lynnworth et al. | 310/335 X |

FOREIGN PATENT DOCUMENTS 55-122146 9/1980 Japan ....................................... 73/632

OTHER PUBLICATIONS

Krautkramer, Josef and Herbert; Ultrasonic Testing of Materials, 1977, pp. 146, 147, 298–301.
Lynworth; Industrial Applications of Ultrasound etc., Mar. 1975; IEEE Transactions on Ultrasonics Ud. 54–22, No. 2, pp. 79, 80.
An Ultrasonic Focusing Transducer, by Rozhdestvenskaya et al., Published Mar. 1979, in Scientific-Research Inst. of Intro. Moscow.

*Primary Examiner*—Steven L. Stephan
*Assistant Examiner*—David V. Carlson

[57] ABSTRACT

A pulse-echo device for obtaining information about a flowing fluid in which a transducer unit comprises an electrically-shielded transducer with a lens for three-dimensionally focusing energy waves, which unit can be inserted into a hole extending through the sidewall of a pipe so that the energy waves focused by the lens are directed across the flow through the pipe. The transducer is surrounded by two electrically-grounded shields which are insulated from each other and separately grounded to isolate the transducer from stray electrical pulses.

5 Claims, 3 Drawing Figures

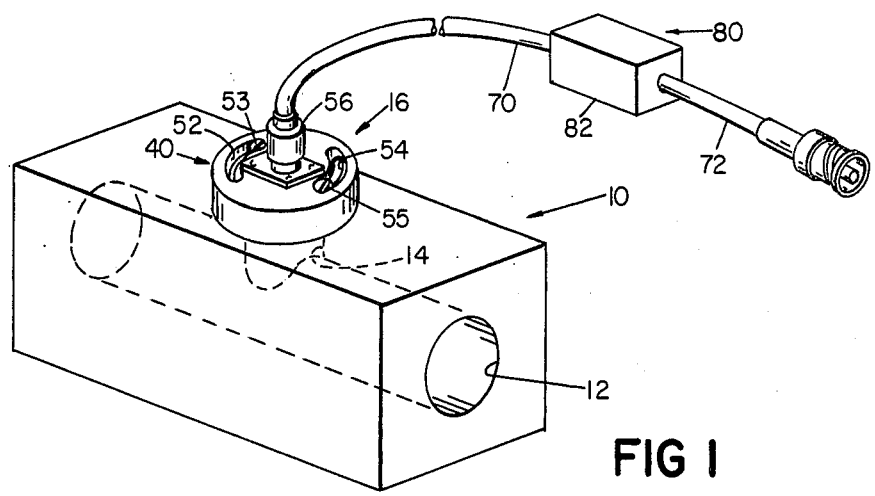
FIG 1
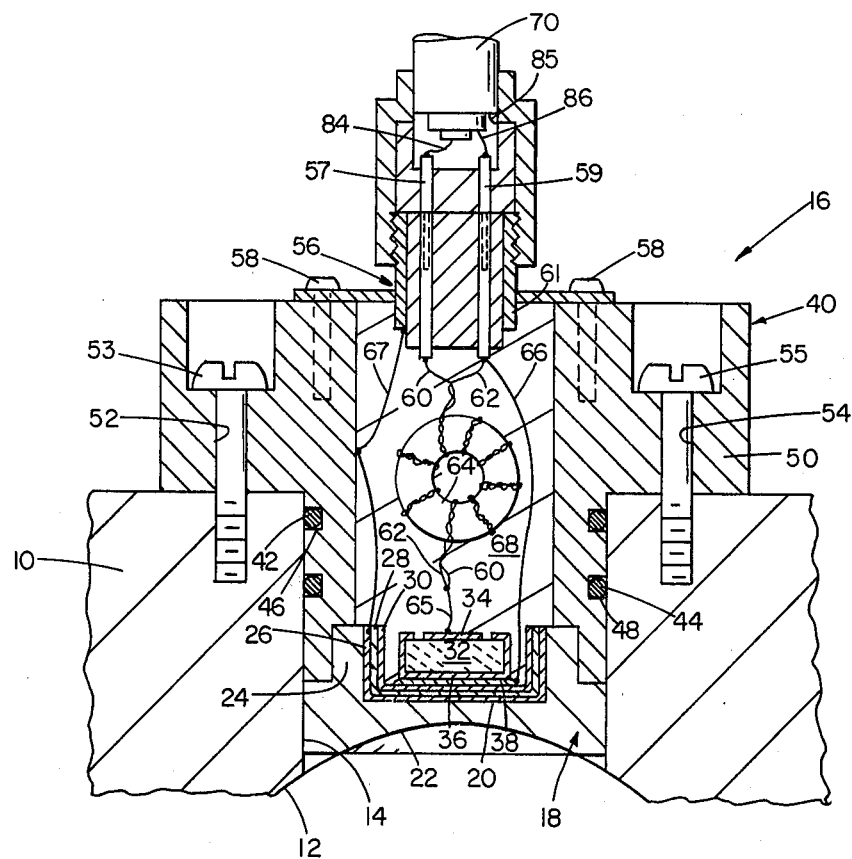
FIG 2
FIG 3

ULTRASONIC SENSING

FIELD OF THE INVENTION

This invention relates to obtaining information about flowing fluid streams, for example, the existence of discontinuities in the fluid or the composition of the fluid.

BACKGROUND OF THE INVENTION

The background of this invention pertaining to the detection of discontinuities in a flowing fluid stream is fully set out in my U.S. Pat. Nos. 4,112,773, and 4,214,484, both hereby incorporated by reference. The background pertaining to obtaining information about the composition of the fluid is set out in my U.S. Pat. application Ser. No. 136,169, filed Mar. 31, 1980, also hereby incorporated by reference.

It is desirable to be able to connect an ultrasonic transmitter-receiver to a pipeline without the need for replacing a portion of the pipeline to ensure proper sound impedance matching. It is also desirable to provide a three-dimensionally focused beam across the flow.

SUMMARY OF THE INVENTION

I have discovered that an ultrasonic transmitter-receiver can be made in the form of an electrically-shielded cylindrical unit, which unit can be inserted into a hole in the sidewall of an existing pipeline so as to direct ultrasonic energy across the flow therethrough. I have further discovered that the beam from the crystal in the unit can be focused three-dimensionally by attaching a concave lens below the crystal.

In preferred embodiments, the bottom and inside sidewalls of a hollow cylinder are coated with a thin layer of electrically conductive paint, which layer is grounded. A cylindrical crystal, electrically isolated from the grounded layer, is mounted inside the cylinder above a concave lens. A metal cap is placed over the crystal and electrically connected to the grounded conductive layer. The unit is then secured in a hole drilled through a pipe sidewall so that energy from the crystal is focused by the lens and directed across the bore of the pipe.

PREFERRED EMBODIMENTS

We turn now to the structure and operation of a preferred embodiment, after first briefly describing the drawings.

Drawings

FIG. 1 is a perspective view of the ultrasonic transmitter-receiver of this invention in place in a pipeline;

FIG. 2 is an enlarged cross-sectional view of the ultrasonic transmitter-receiver; and FIG. 3 is a view of a step-up transformer with a portion broken away.

STRUCTURE

Referring to FIG. 1, there is shown a pipe 10 having an interior bore 12. A hole 14 extends through the sidewall of the pipe 10 to the bore 12. Ultrasonic transmitter-receiver 16 is mounted in the hole 14.

As shown in FIG. 2, ultrasonic transmitter-receiver 16 comprises a lower lens portion 18 and an aluminum cap 40. Lower lens portion 18, which is made of methyl methacrylate, has a flat circular surface 20 disposed above a three-dimensionally concave lens 22. The radius of the concavity is 1½ inches. Surface 20 is surrounded by a cylindrical sidewall 24. Surface 20 and the inside of the sidewall 24 are coated with a first thin layer 26 of electrically conductive silver paint. A thin layer 28 of non-conductive epoxy covers the first conductive layer 26. The non-conductive layer 28 is coated with a second layer 30 of electrically conductive paint. All three layers are shown enlarged in FIG. 2. A suitable paint is DuPont Conductor Composition 907770 Butyl Acetate, and Araldite is a suitable non-conductive epoxy.

A piezoelectric crystal 32 is mounted above the surface 20. Crystal 32 is cylindrical with a diameter of ½ inch. Crystal 32 has an upper electrode 34 and a lower electrode 36. Upper electrode 34 is circular and has a diameter of about ⅜ inches. Lower electrode 36 covers the entire lower surface and sides of the crystal 32. A small portion of the lower electrode 36 extends over the upper surface of the crystal to within 1/32 of an inch of the upper electrode 34. Conductive epoxy 38 electrically connects the lower electrode 36 to the second conductive layer 30. The crystal 32 is a 10 MHz Lithium-Niobate circular crystal, available from Valpey-Fisher Company of Hopkington, Mass. The epoxy 38 is Stycyst 1970.

The lower portion of the metal cap 40 force fits around the outside of sidewall 24 of the lens portion 18. A pair of O-ring seals 42, 44 are disposed in a corresponding pair of annular grooves 46, 48 around the outside of cap 40. A flange 50 extends around the top of cap 40. Flange 50 has a pair of combination screw holes and slots 52, 54 therethrough, which receive screws 53, 55 attached to the pipe 10.

A twinax Amphanol connector 56 is attached to the top of cap 40 by screws 58. A hot wire 60 from a hot pin 57 of connector 56 is attached to the upper electrode 34 on the crystal 32. A second wire 62 from the upper electrode 34 is connected to an inner ground shield 59 of the twinax connector 56. Both wires 60, 62 are twisted together and wrapped eight times around a toroid 64.. Toroid 64 is a toroid core 266T125/3E2A from Ferrox Cube of Saugertise, N.Y.

A second ground wire 66 from the lower electrode 36 is connected to the inner ground shield 59 of the connector 56, and a third ground wire 67 is connected from the first layer 26 of conductive paint to the metal cap 40 and an outer ground shield 61 of the connector 56.

An epoxy backing 68 covers the crystal 32 and fills the cap 40. The epoxy backing is tungsten-loaded Araldite mixed with a polyamide hardener. The ratio of epoxy to tungsten for the backing 68 is 1:1 by weight.

One end of twinax cable 70 is connected to the twinax connector 56, and the other end is connected to a transformer 80. As best shown in FIG. 3, transformer 80 comprises a box 82 in which a wire 84 from the hot pin 57 of the connector 56 is wrapped around a toroid 88 and connected to a wire 86 from the inner ground shield 59. A wire 85 from the outer ground shield is also connected to wire 86 inside the box 80. The toroid 88 is the same type as toroid 64. A coaxial cable 72 enters the other side of the box 82, and its hot wire 74 is similarly wrapped around the toroid 88 and connected to a wire 75 from its inner ground shield. The other end of cable 72 is connected to the electronic devices (not shown), which are preferably the same as those described in my U.S. Patent application Ser. No. 136,169, filed Mar. 31, 1980. The box 82 is a Pamona Electric Company of California Box No. 3752, and it is filled with Araldite epoxy 87.

OPERATION

In operation, the hole 14 is drilled through the sidewall of the pipe which will contain the flow to be monitored. The ultrasonic transmitter-receiver 16 is then fit into hole 14 until the bottom edge of the lens 22 is almost through the pipe 10 and into the bore 12. The O-ring seals 42, 44 prevent leakage between the hole 14 and the cap 40. Screws 53, 55 fit through the screw holes of the flange 50 and hold the ultrasonic transmitter-receiver 16 in place when the ultrasonic transmitter-receiver 16 is rotated so the screw shafts fit into the corresponding slots, which are too narow to allow the screw heads to pass therethrough. When the cable 72 is connected to the electronics, the first conductive layer 26 and the metal cap 40 are grounded, and this shields the crystal 32 from outside interference. The toroid 64 with its wrapped wires 60, 62 matches the electrical impedance for both the crystal 32 and the twinax cable 70. The transformer unit 80 provides the crystal 32 with an improved signal.

The device is then operated as described in my U.S. Patent application Ser. No. 136,169, filed Mar. 31, 1980, with the lens 22 three-dimensionally focusing the ultrasonic beam from the crystal 32.

OTHER EMBODIMENTS

The hole need not extend all the way through the sidewall of the pipe if the pipe material, i.e., methyl methacrylate or steel, can be sound impedance matched with the lens portion 18 of the unit. In that case, the lens portion 18 can be mounted in a blind hole in the pipe sidewall and coupled thereto with stopcock grease. Similarly, it is also possible under these conditions to omit the blind hole and attach the unit directly to the side of the pipe.

Also, the lower lens portion may be extended and made of quartz or sapphire to separate the crystal from a flow of hot material, i.e., liquid metal. In this case, the extended lens portion with the lens on its end away from the crystal forms a buffer rod which conducts sound but not heat.

Other embodiments of the invention will occur to those skilled in the art.

What is claimed is:

1. A pulse-echo device for obtaining information about a fluid, said device being adapted to fit into a hole extending through the sidewall of a conduit, comprising:
   a transducer unit,
   said transducer unit having a transducer for producing energy waves,
   said transducer having a first and a second electrode,
   said transducer also having a first electrically-grounded shield which isolates said transducer from the fluid in the conduit and a second electrically-grounded shield which is separated from said first shield and which completely surrounds said transducer,
   at least a portion of said transducer unit being adapted to connect to a pipe so as to direct the focused energy waves into fluid flowing through the conduit.

2. The device of claim 1 wherein said transducer unit has a lens, which said lens is concave and focuses the energy waves three-dimensionally.

3. The device of claim 1 wherein said second shield partially comprises a grounded metal cap, said cap being disposed over the top of said transducer.

4. The device of claim 1 wherein said transducer unit further comprises a holding element which supports said transducer, and a lens disposed below said holding element, which element is adapted to fit into the hole through the sidewall of the conduit.

5. The device of claim 4 wherein said lens is made of sapphire.

* * * * *